US00PP29760P3

(12) United States Plant Patent
Grice

(10) Patent No.: US PP29,760 P3
(45) Date of Patent: Oct. 16, 2018

(54) ***CALIBRACHOA* PLANT NAMED 'JGCAL09404'**

(50) Latin Name: ***Calibrachoa* sp.**
Varietal Denomination: JGCAL09404

(71) Applicant: PLANT 21 LLC, Bonsall, CA (US)

(72) Inventor: Jessica Grice, Bonsall, CA (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/530,656

(22) Filed: Feb. 16, 2017

(65) Prior Publication Data

US 2018/0235132 P1 Aug. 16, 2018

(51) Int. Cl.
*A01H 5/02* (2018.01)

(52) U.S. Cl.
USPC ..... Plt./413

(58) Field of Classification Search
USPC ..... Plt./413

CPC . A01H 5/02; A01H 5/025; A01H 5/12; A01H 5/00

See application file for complete search history.

(56) References Cited

PUBLICATIONS

Pleasant View Gardens Grower Resource Guide 2016-2017, retrieved on Mar. 8, 2018, retrieved from the Internet at http://www.pvg.com/splash/2016_PVG_Catagog_LR.pdf, cover page, pp. 10,48-49,54-55,86,107-108,110,266-271,276,283,back cover. (Year: 2016).*

* cited by examiner

*Primary Examiner* — June Hwu
(74) *Attorney, Agent, or Firm* — C. A. Whealy

(57) ABSTRACT

A new and distinct *Calibrachoa* plant named 'JGCAL09404', characterized by its upright to outwardly spreading and mounding to eventually trailing plant habit; moderately vigorous to vigorous growth habit; freely branching habit; dense and bushy appearance; freely flowering habit; large dark violet and close to black-colored petals with yellow-colored centers; and good garden performance.

1 Drawing Sheet

Botanical designation: *Calibrachoa* sp.
Cultivar denomination: 'JGCAL09404'.

BACKGROUND OF THE INVENTION

The present invention relates to a new and distinct cultivar of *Calibrachoa* plant, botanically known as *Calibrachoa* sp. and hereinafter referred to by the name 'JGCAL09404'.

The new *Calibrachoa* plant is a product of a planned breeding program conducted by the Inventor in Bonsall, Calif. The objective of the breeding program is to create new uniform and freely-branching *Calibrachoa* plants with unique and attractive flower coloration, good garden performance and resistance to pathogens.

The new *Calibrachoa* plant originated from a cross-pollination conducted by the Inventor in Bonsall, Calif. on Sep. 11, 2013 of *Calibrachoa* sp. 'Duealkomidbu', disclosed in U.S. Plant Pat. No. 25,487, as the female, or seed, parent with a proprietary selection of *Calibrachoa* sp. identified as code number 11C110-02, not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on Jul. 9, 2014.

Asexual reproduction of the new *Calibrachoa* plant by vegetative terminal cuttings in a controlled greenhouse environment in Bonsall, Calif. since Jul. 15, 2014 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JGCAL09404'. These characteristics in combination distinguish 'JGCAL09404' as a new and distinct *Calibrachoa* plant:

1. Upright to outwardly spreading and mounding to eventually trailing plant habit.
2. Moderately vigorous to vigorous growth habit.
3. Freely branching habit; dense and bushy appearance.
4. Freely flowering habit.
5. Large dark violet and close to black-colored petals with yellow-colored centers.
6. Good garden performance.

The new *Calibrachoa* plant can be compared to plants of the female parent, 'Duealkomidbu'. Plants of the new *Calibrachoa* differ primarily from plants of 'Duealkomidbu' in flower size as plants of 'Duealkomidbu' have smaller flowers. In addition, plants of the new *Calibrachoa* root faster and are more resistant to root pathogens than plants of 'Duealkomidbu'.

The new *Calibrachoa* plant can be compared to plants of the male parent selection. Plants of the new *Calibrachoa* differ primarily from plants of the male parent selection in flower color as plants of the male parent selection have black, yellow and red-colored petals. In addition, plants of the new *Calibrachoa* have larger flowers, root faster and are more resistant to root pathogens than plants of the male parent selection.

Plants of the new *Calibrachoa* can be compared to plants of the *Calibrachoa* sp. 'USCAL84704', disclosed in U.S. Plant Pat. No. 23,231. In side-by-side comparisons, plants of the new *Calibrachoa* differ primarily from plants of 'USCAL84704' in flower size as plants of 'USCAL84704' have smaller flowers. In addition, plants of the new *Calibrachoa* root faster and are more resistant to root pathogens than plants of 'USCAL84704'.

Plants of the new *Calibrachoa* can be compared to plants of the *Calibrachoa* sp. 'USCAL68604', disclosed in U.S. Plant Pat. No. 22,964. In side-by-side comparisons, plants of the new *Calibrachoa* differ primarily from plants of 'USCAL68604' in flower size as plants of 'USCAL68604' have smaller flowers. In addition, plants of the new *Calibrachoa* root faster and are more resistant to root pathogens than plants of 'USCAL68604'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'JGCAL09404' grown in a container.

The photograph at the top of the sheet is a close-up view of a typical flowering plant of 'JGCAL09404'.

DETAILED BOTANICAL DESCRIPTION

The aforementioned photographs and following observations and measurements describe plants grown during the spring in 10-cm containers in an acrylic-covered greenhouse in Carleton, Mich. and under cultural practices typical of commercial *Calibrachoa* production. During the production of the plants, day and night temperatures ranged from 18° C. to 30° C. Plants were six weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'JGCAL09404'.

Parentage:

- *Female, or seed, parent.*—*Calibrachoa* sp. 'Duealkomidbu', disclosed in U.S. Plant Pat. No. 25,487.
- *Male, or pollen, parent.*—Proprietary selection of *Calibrachoa* sp. identified as code number 11C110-02, not patented.

Propagation:

- *Type.*—By vegetative terminal cuttings.
- *Time to initiate roots, summer.*—About four days at temperatures ranging from 17° C. to 29° C.
- *Time to initiate roots, winter.*—About six days at temperatures ranging from 17° C. to 21° C.
- *Time to produce a rooted plant, summer.*—About 22 days at temperatures ranging from 17° C. to 29° C.
- *Time to produce a rooted plant, winter.*—About 25 days at temperatures ranging from 17° C. to 21° C.
- *Root description.*—Medium in thickness, fibrous; typically white in color, actual color of the roots is dependent on substrate composition, water quality, fertilizer type and formulation, substrate temperature and physiological age of roots.
- *Rooting habit.*—Freely branching; medium density.

Plant description:

- *Plant and growth habit.*—Upright to outwardly spreading and mounding to eventually trailing plant habit; moderately vigorous to vigorous growth habit; moderate growth rate; freely branching habit with about three to four primary lateral branches each with about four secondary branches; dense and bushy appearance.
- *Plant height.*—About 15.3 cm.
- *Plant diameter.*—About 24 cm by 25 cm.

Lateral branch description:

- *Length.*—About 14 cm.
- *Diameter.*—About 2 mm.
- *Internode length.*—About 1.2 cm.
- *Strength.*—Strong.
- *Aspect.*—Initially upright then outwardly spreading to eventually trailing.
- *Texture and luster.*—Pubescent; matte.
- *Color, developing.*—Close to 145A.
- *Color, developed.*—Close to 146B.

Leaf description:

- *Arrangement.*—Before flowering, alternate; after flowering, opposite; leaves simple.
- *Length.*—About 2.7 cm.
- *Width.*—About 1 cm.
- *Shape.*—Elliptical.
- *Apex.*—Broadly acute.
- *Base.*—Attenuate.
- *Margin.*—Entire.
- *Texture and luster, upper and lower surfaces.*—Pubescent, minute; matte.
- *Venation pattern.*—Pinnate; arcuate.
- *Color.*—Developing leaves, upper surface: Close to 146A. Developing leaves, lower surface: Close to 146B. Fully expanded leaves, upper surface: Close to N137C; venation, close to 146C. Fully expanded leaves, lower surface: Close to 147B; venation, close to 146B.
- *Petioles.*—Length: About 5 mm. Diameter: About 2 mm. Texture and luster, upper and lower surfaces: Pubescent, minute; matte. Color, upper and lower surfaces: Close to 146C.

Flower description:

- *Flower type and flowering habit.*—Single salverform flowers arising from leaf axils; freely flowering habit with typically about 180 flowers and flower buds developing per plant; flowers face upright to outwardly.
- *Fragrance.*—None detected.
- *Natural flowering season.*—Plants of the new *Calibrachoa* begin flowering about six weeks after planting; plants flower continuously from the spring though the summer until frost.
- *Flower longevity.*—Individual flowers last about one week on the plant; flowers persistent.

*Flower buds*.—Length: About 2.6 cm. Diameter: About 8 mm. Shape: Oblong, elongate. Texture and luster: Pubescent, minute; matte. Color: Close to 195B.

*Flower diameter*.—Large, about 4.2 cm by 4.2 cm.

*Flower length* (*height*).—About 3 cm.

*Flower throat diameter*.—About 6 mm by 8 mm.

*Flower tube length*.—About 2.3 cm.

*Flower tube diameter*.—Proximally, about 3 mm; distally, about 1.2 cm.

*Corolla*.—Arrangement: Five fused petals opening into a flared trumpet. Petal lobe length (from throat): About 1.7 cm. Petal lobe width: About 2 cm. Petal shape: Fan-shaped. Petal apex: Emarginate; moderately lobed. Petal margin: Entire; moderately undulate and reflexing. Petal texture and luster, upper surface: Smooth, glabrous, velvety; matte. Petal texture and luster, lower surface: Pubescent, minute; matte. Throat texture and luster: Smooth, glabrous; matte. Tube texture and luster: Pubescent, minute and primarily along the veins; matte. Color: Petal lobe, when opening, upper surface: Close to 86B. Petal lobe, when opening, lower surface: Close to N200D. Petal lobe, fully opened, upper surface: Ground color, close to brighter than 86A; large wide band surrounding the throat, close to N186A; venation, close to 79A, moderately strong to strongly conspicuous; with development, ground color becoming closer to 86B. Petal lobe, fully opened, lower surface: Close to 79B; venation, close to N79A; with development, color becoming closer to 79C to 79D. Throat: Close to 12B; venation, strongly conspicuous, close to 183B. Tube: Close to 160D; venation, close to 187B.

*Calyx*.—Arrangement: One star-shaped calyx tube with five sepals fused towards the base and arranged in a single whorl. Length: About 1.6 cm. Diameter: About 1.5 cm. Sepal length: About 1 cm. Sepal width: About 3 mm. Sepal shape: Lanceolate. Sepal apex: Acute. Sepal margin: Entire. Sepal texture and luster, upper and lower surfaces: Pubescent, minute; matte. Sepal color, upper surface: Close to 146A. Sepal color, lower surface: Close to 146B.

*Peduncles*.—Length: About 2.2 cm. Diameter: About 1 mm. Angle: About 30° to 45° from stem axis. Strength: Strong. Texture and luster: Pubescent, minute; matte. Color: Close to 146B.

*Reproductive organs*.—Stamens: Quantity: Five per flower. Filament length: About 1 cm. Filament color: Close to 145C. Anther size: About 1 mm by 1 mm. Anther shape: Round. Anther color: Close to 8B. Pollen amount: Moderate. Pollen color: Close to 9A. Pistils: Quantity: One per flower. Pistil length: About 9 mm. Style length: About 8 mm. Style color: Close to 145B. Stigma diameter: About 1 mm. Stigma shape: Oval. Stigma color: Close to 146A. Ovary color: Close to 145B. Seeds and fruits: Seed and fruit development have not been observed on plants of the new *Calibrachoa*.

Garden performance: Plants of the new *Calibrachoa* have been observed to have good garden performance and tolerate wind, rain and to be suitable for USDA Hardiness Zones 9 to 11.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'JGCAL09404' as illustrated and described.

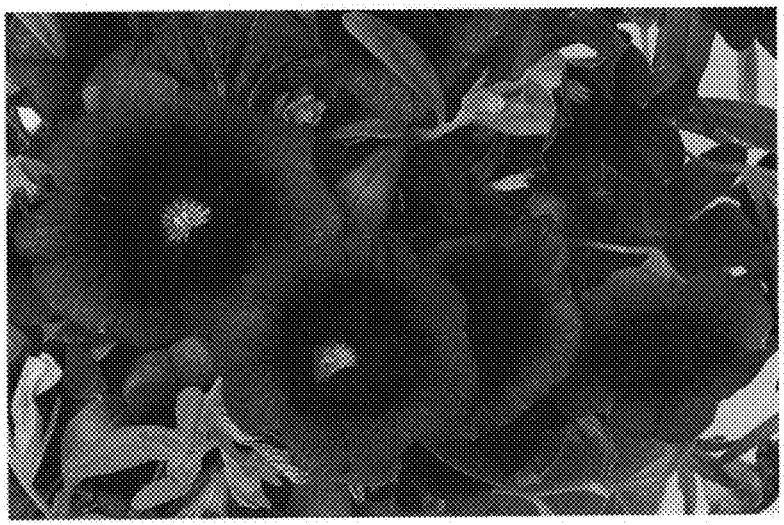
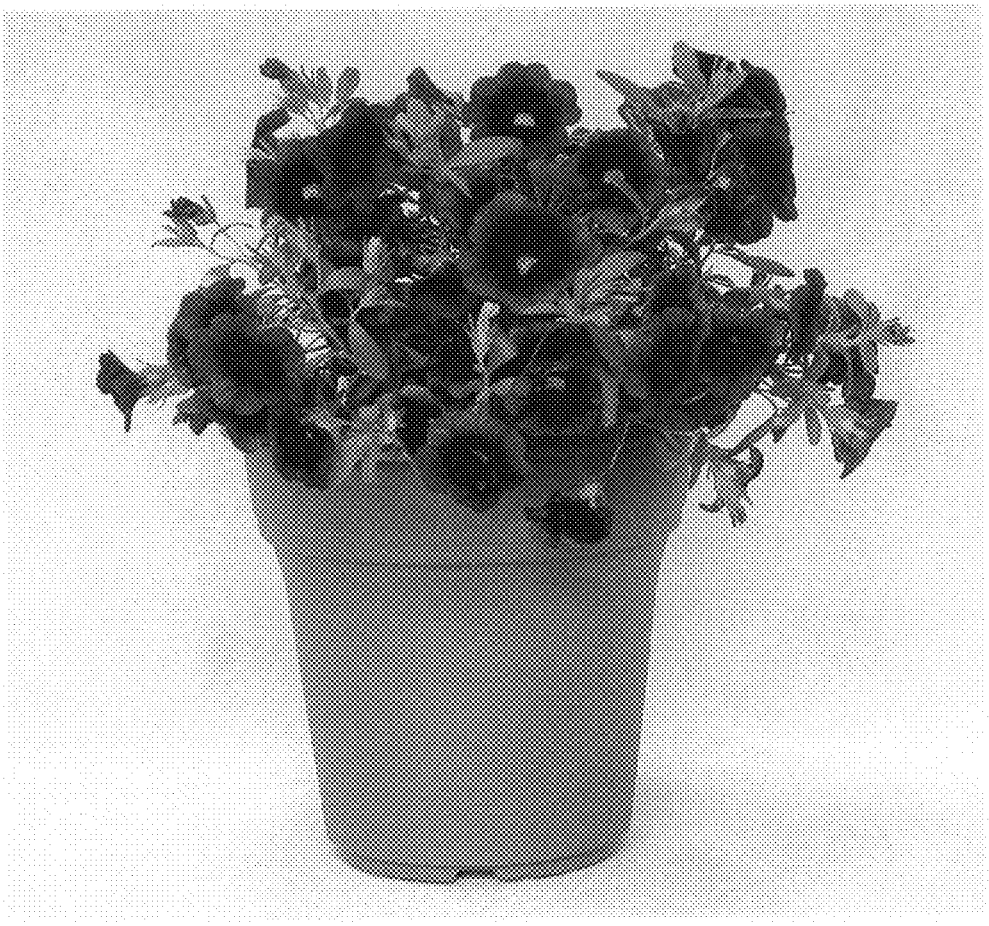

* * * * *